United States Patent
Hannapel et al.

(10) Patent No.: US 9,987,102 B2
(45) Date of Patent: Jun. 5, 2018

(54) ORTHODONTIC PROTECTION DEVICE

(71) Applicant: ORVANCE, LLC, Alto, MI (US)

(72) Inventors: Eric D. Hannapel, Middleville, MI (US); David Gerard Jablonski, Alto, MI (US)

(73) Assignee: OrVance, LLC, Caledonia, MI (US)

( * ) Notice: Subject to any disclaimer, the term of this patent is extended or adjusted under 35 U.S.C. 154(b) by 1031 days.

(21) Appl. No.: 14/273,494

(22) Filed: May 8, 2014

(65) Prior Publication Data

US 2015/0209120 A1    Jul. 30, 2015

Related U.S. Application Data (60) Provisional application No. 61/933,542, filed on Jan. 30, 2014.

(51) Int. Cl.
*A61C 7/12* (2006.01)
*A63B 71/08* (2006.01)

(52) U.S. Cl.
CPC ............ *A61C 7/125* (2013.01); *A63B 71/085* (2013.01)

(58) Field of Classification Search
CPC .............. A63B 71/085; A63B 2208/12; A63B 2071/088; A63B 2071/086; A63B 2209/02; A61F 5/566; A61F 5/56; A61F 5/50; A61F 5/58; A61C 7/08; A61C 5/14; A61B 13/00; A61B 1/24
See application file for complete search history.

(56) References Cited

U.S. PATENT DOCUMENTS

| | | | |
|---|---|---|---|
| 3,455,872 A | 7/1969 | Beck | |
| 4,497,926 A | 2/1985 | Toy | |
| 5,624,745 A | 4/1997 | Lapidus | |
| 6,638,881 B2 | 10/2003 | Lapidus | |
| 7,195,484 B1 | 3/2007 | Wagner | |
| 7,312,256 B2 | 12/2007 | Borja | |
| 7,789,662 B2 * | 9/2010 | Van Eikeren | A61C 5/90 433/136 |
| 8,007,277 B2 | 8/2011 | Fischer | |
| 2003/0205234 A1 | 11/2003 | Bardach | |
| 2005/0089820 A1 * | 4/2005 | Allred | A61C 5/00 433/215 |
| 2005/0181324 A1 | 8/2005 | Hare | |
| 2005/0239015 A1 | 10/2005 | Dragan | |
| 2006/0063128 A1 | 3/2006 | Dragan | |

(Continued)

FOREIGN PATENT DOCUMENTS

| | | |
|---|---|---|
| CA | 2858830 A1 | 6/2013 |
| EP | 2544651 A1 | 1/2013 |
| WO | 2011112193 A1 | 9/2011 |

*Primary Examiner* — Ophelia A Hawthorne
(74) *Attorney, Agent, or Firm* — Nyemaster Goode, P.C.

(57) ABSTRACT

An easily applied device is described that protects the soft tissues inside of the mouth from abrasion by orthodontic braces. The device consists of a putty-like, moldable material that may be pressed onto and into and molded about the brackets and wires of orthodontic braces, and a plasticized and dehydrated or partially dehydrated hydrogel-forming layer on those surfaces of the device that contact the braces and teeth so as to absorb saliva and dry to some extent the surfaces to which the device is pressed and to offer initial adhesion of the device to the teeth and/or braces.

21 Claims, 5 Drawing Sheets

(56) References Cited

U.S. PATENT DOCUMENTS

| | | | |
|---|---|---|---|
| 2007/0015107 A1* | 1/2007 | Mannschedel | A61C 5/42 |
| | | | 433/102 |
| 2007/0185237 A1 | 8/2007 | Rajaiah et al. | |
| 2008/0293015 A1 | 11/2008 | Wong et al. | |
| 2012/0107768 A1 | 5/2012 | Diedwardo | |
| 2012/0199138 A1* | 8/2012 | Hannapel | A61C 7/125 |
| | | | 128/859 |
| 2014/0017637 A1 | 1/2014 | Cinader, Jr. et al. | |
| 2015/0037266 A1 | 2/2015 | Boyd et al. | |

* cited by examiner

ORTHODONTIC PROTECTION DEVICE

CROSS-REFERENCE TO RELATED APPLICATION

This application claims priority from U.S. Provisional Patent Application Ser. No. 61/933,542 filed Jan. 30, 2014, entitled "Orthodontic Protection Device" the entire specification of which is hereby incorporated by reference.

BACKGROUND

Quite a few devices have been described that offer protections of the soft tissues of the mouth from abrasion by orthodontic braces, but all possess significant drawbacks that have prevented their wide use. One device describes a silicone bracket cap with holes and slits that fit over a bracket and is secured by the main wire, requiring the placement of many caps and a bumpy, irregular feel. Another teaches a silicone shield that employs room temperature setting silicone that is placed in the mouth and allowed to set, then removed from the mouth and trimmed, and inconvenient procedure, and sanitary storage must be employed for re-use of the device.

A flat thermoplastic strip has been described that required heating to between 160-212 degrees Fahrenheit to soften it, whereupon it is pressed onto and molded onto the teeth and braces. A moldable lip guard has been described that must first be heated in hot water. Another disclosure teaches a two-part curable silicone composition that, upon mixing the parts, yields a putty-like consistency that can be molded over the braces before the cure is complete. The mixing and timing aspects of this device also render it inconvenient to use.

A putty-like, moldable material, a product currently on the market, comes in small strips that can be pressed onto the braces to offer protection. This material is a silicone high consistency rubber (HCR) base, well known to those practiced in the art of silicones. However, even when molded onto and into the brackets and wires of orthodontic braces, it adheres poorly if the braces are moist with saliva. Unfortunately, braces are typically very moist with saliva since the presence of braces in the mouth commonly stimulates its excess production, the saliva then acting as a lubricant such that even though molded into and onto the brackets and wires of the braces, the material easily dislodges from the braces. Hence the instructions state "Your brackets must be completely dry for Silicone wax to adhere properly." This is a difficult state to achieve.

In addition, this material tends to stick more aggressively to the fingers than to the braces if the braces are wet and the fingers are dry, causing the material to pull off the braces during attempted application. What is required is a device that offers protection of the soft tissues of the mouth from abrasion by orthodontic braces that is extremely convenient to use (for example, does not require heating or curing), will work well in a situation where the braces are very wet with saliva, will adhere upon application more aggressively to wet teeth and braces than to dry fingers, and will remain in position during activities such as play, participation in sports, while playing musical instruments that require the mouth, drinking, and eating.

SUMMARY

An orthodontic protection device comprises a protective layer shaped to fit over the facial surface of a user's teeth and composed substantially of a moldable material, and an adhesive layer including at least one hygroscopic polymeric material.

A method of fabricating an orthodontic protection device comprises molding or extruding a moldable material and coating one or more surfaces of the moldable material with an adhesive layer which includes a hygroscopic polymer. In some instances the method also includes dehydrating the adhesive layer.

BRIEF DESCRIPTION OF THE DRAWINGS

Various features will become apparent to those skilled in the art from the following detailed description of the disclosed non-limiting disclosure. The drawings that accompany the detailed description can be briefly described as follows.

DETAILED DESCRIPTION

An orthodontic appliance shield or guard is disclosed in the form of a flexible guard or shield which is easily installed over an orthodontic appliance and which protects the surrounding inner soft lip and cheek tissue from contact with the sharp surfaces of the orthodontic appliance if the user's face is accidently struck, with force, such as during an athletic event. This minimizes the occurrence of cuts and bleeding in the lips and cheeks, which require the athlete to be removed from the athletic contest until the bleeding stops. The orthodontic appliance shield is easy to install and provides a one time, inexpensive, disposable use; while, at the same time, protecting the soft tissue in a user's mouth surrounding the orthodontic appliance from injury during physical contact in an athletic event.

Figure 1:
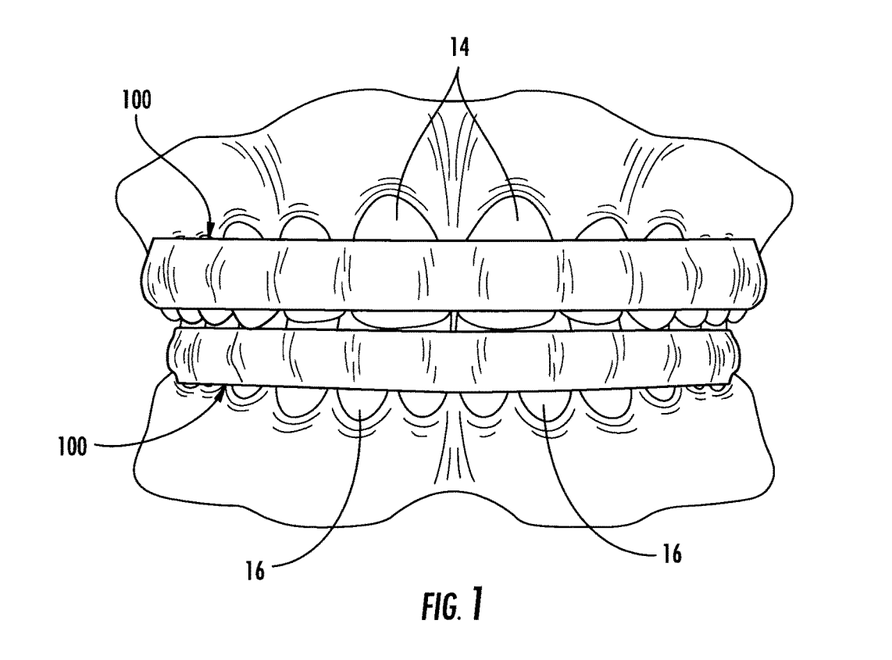
FIG. 1 is a pictorial representation showing the installation of orthodontic appliance guards on both upper and lower sets of teeth.

Referring to FIG. 1, there is a depicted an example of orthodontic protection device applied to either or both of a user's upper teeth 14 and lower teeth 16, respectively. It will be understood that the shape, attachment, length and number of teeth to which the orthodontic protection device 100 is applied is shown in FIG. 1 only by way of example as it will be understood that the orthodontic protection device 100 may take any necessary shape and configuration to suit a particular user's orthodontic requirements.

The orthodontic protection device 100, shown in FIGS. 1-4, is formed of an elongated strip of pliable, flexible material which is sized in width to cover the entire exterior surface of the orthodontic appliances. Although the orthodontic protection device 100 is shown in FIG. 1 as being applied over both of the orthodontic appliances (braces) affixed to the upper teeth 14 and the lower teeth 16 of a user, a single orthodontic protection device 100 can be provided for the upper teeth 14 or for the lower teeth 16 of the user.

Figure 4:
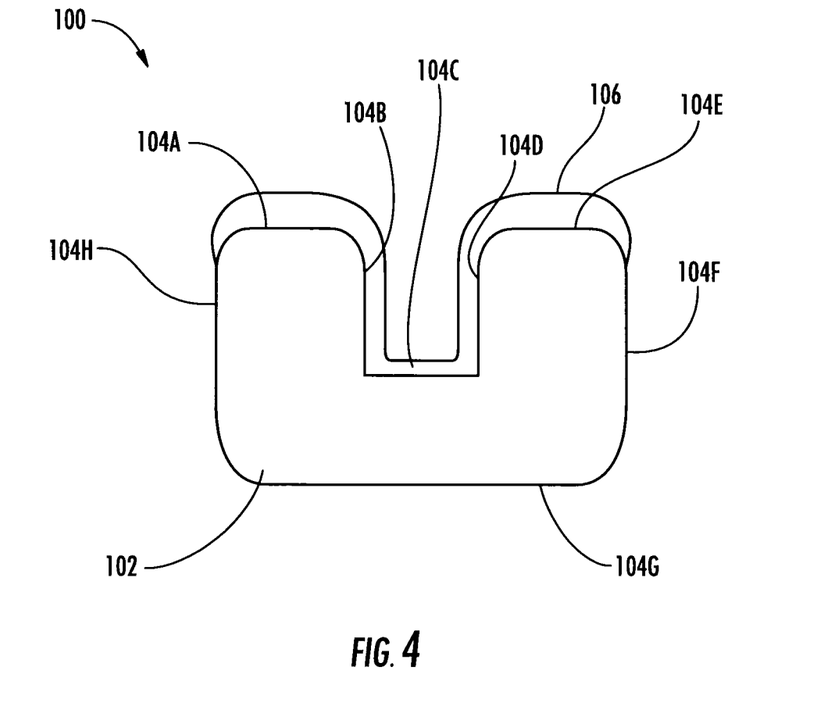
FIG. 4 is a side cross-sectional view of a variant of a device of the type shown in FIG. 2
Figure 4A:
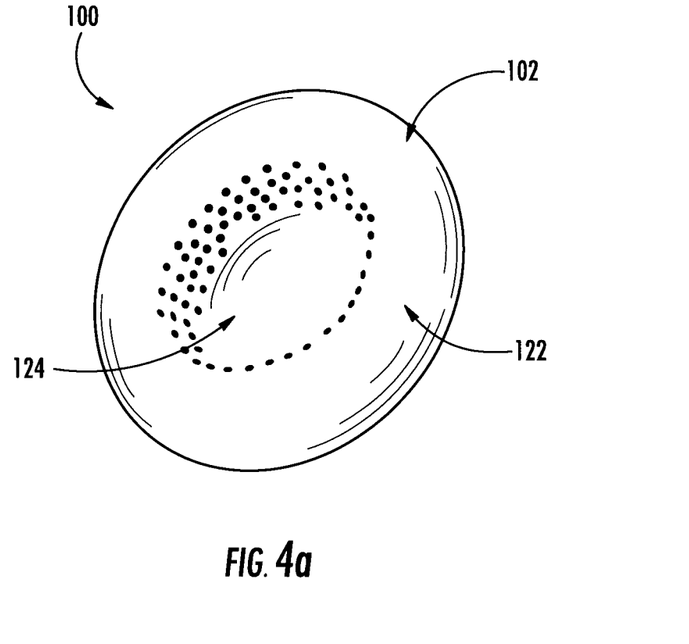
FIG. 4a is a perspective view of a variant of a device having a circular configuration instead of an elongated configuration.

Additionally, with reference to FIG. 4a, other shapes are contemplated such as, circular or other dish-like configurations having a varying perimeter structure (such as circular, oval, elliptical, polygonal, or arbitrary).

The present disclosure is directed to devices for temporarily coating intra-oral, orthodontic implements (e.g., orthodontic brackets and/or arch wires) to reduce discomfort and prevent injury to the soft tissues within a user's mouth. The present disclosure is further directed toward methods of fabricating such devices.

Figure 2:
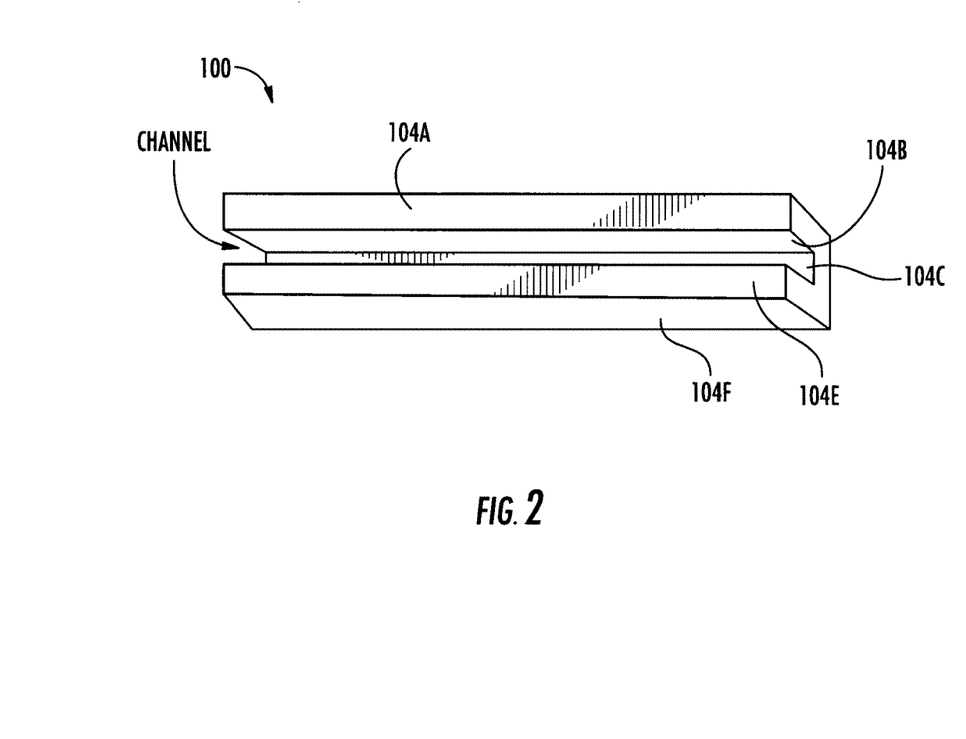
FIG. 2 is a perspective view of another aspect of an orthodontic protection device according to the present disclosure.
Figure 3:
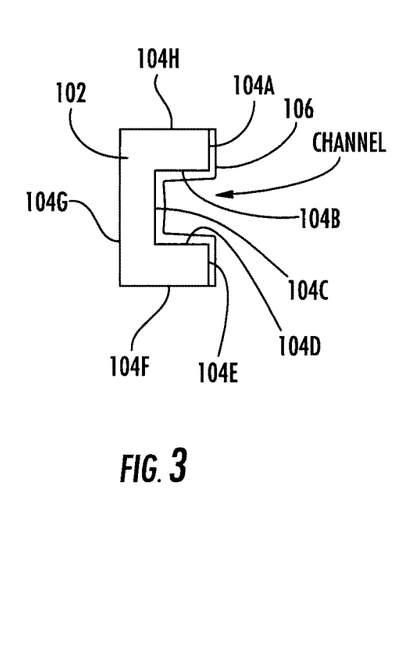
FIG. 3 is an end view of the device shown in FIG. 2.

FIGS. 2 and 3 show a side cross-sectional view and a perspective view of one variation of a device 100 which can be adhered to the facial surfaces of a user's teeth, and/or to any orthodontic implements attached to the user's teeth, to minimize discomfort to the user or minimize damage to the user's soft tissues resulting from an orthodontic implement. Device 100 includes a protective layer 102 composed substantially of a moldable material. The moldable material can in certain variations be formed in a shape suitable to accommodate an orthodontic implement disposed in a user's mouth. For example, with the embodiment of FIG. 4a, the protective layer 102 includes an outer rim region (i.e., annular wall) 122 and a cavity region 124 defined thereby.

As used herein, the phrase "moldable material" refers to any material that is substantially plastically deformable at a temperature equal to or less than about 37° C. and under a stress reasonably applied by manual pressure. As such, the moldable material can possess viscoelastic properties, viscoplastic properties, thermoplastic properties, or any other molecular properties which confer the desired moldability.

In some variations, the moldable material can comprise a polymeric material. As used herein, a polymeric material can include any material whose molecular structure comprises at least ten covalently attached monomeric subunits, each monomeric subunit having similar structure. Plastic properties of a suitable polymeric can be modified, for example, by cross-linking. In some particular instances, the moldable material can comprise a silicone polymer. Suitable examples of moldable material can include, but are not limited to, thermoplastic elastomers (plasticized and non-plasticized) having glass transition temperatures below body temperature (approximately 37° C.); viscoelastic silicone rubber; polydimethylsiloxane combined with fumed silica or trimethylsilylated silica filler; and a mixture of polydimethylsiloxane and vinyl-functionalized polydimethylsiloxane combined with fumed silica or trimethylsilylated silica filler. The latter material is well known to those practiced in the art of silicone chemistry and is referred to as silicone High Consistency Rubber (HCR) base. Among other examples, the moldable material may comprise, but is not limited to Dow Corning Silastic Q7-4535, Q7-4550, and Q7-4565 Biomedical Grade ETR Elastomer, Wacker Elastosil R Plus 4000/50 Silicone Rubber Base; Wacker Elastosil R 401/50 S Silicone Rubber Base, and NuSil MED-4174 Silicone Elastomer.

As shown in this example, device 100 can include eight (8) surfaces 104A, 104B, 104C, 104D, 104E, 104F, 104G, and 104H. Surfaces 104A, 104B, 104C, 104D, and 104E together form what may be termed a dental contacting surface. Device 100 further includes and adhesive layer 106 which coats at least a portion of device 100 surfaces. In the device of FIG. 4a, a similar cross-sectional configuration is envisioned, with surfaces 104C, 104D being the same annular surface, and the surfaces 104F and 104H being the same outer annular surface. Such a device may have a diameter of, for example 6 mm (while not being limited thereto), so as to fit over a generally localized area.

The device 100 in FIG. 2 shows surfaces 104A, 104B, 104C, 104E, and 104F visible. The perspective view of FIG. 2 illustrates that the shape of device 100 includes an orthodontic accommodation element, in this case an elongated member with a base, and opposing walls that define a longitudinal channel. The interior walls of the extended channel consist of surfaces 104B, 104C, and 104D. When device 100 is employed in a user's mouth, surfaces 104A and 104E may tend to contact the facial surfaces of the user's teeth, while surfaces 104B, 104C, and 104D may tend to contact the surfaces of an orthodontic implement such as orthodontic brackets and/or arch wires. It is important to note that the shape of device 100 shown in FIGS. 2-4 is exemplary only and that in various alternatives, device 100 need not include discrete surfaces 104A, 104B, 104C, 104D, 104E, 104F, 104G, and 104H. The device need only have a shape configured to contact the teeth and orthodontic appliance. In the embodiment of FIG. 4a, an annular wall 122 surrounds and defines a cavity.

The moldable material can be partially or completely coated on at least one surface with an adhesive layer 106 comprising a hygroscopic polymeric material to enable adhesion of the device to a user's teeth and or orthodontic implement(s). In some instances, the hygroscopic polymeric material can be dehydrated prior to use.

As used herein, the term "hygroscopic" can be used to describe a material capable of absorbing at least twice its dry weight in water at standard temperature and pressure. In some instances the term "hygroscopic" can describe a material capable of absorbing at least ten times its dry weight in water at standard temperature and pressure. Suitable hygroscopic polymeric materials can include, but are not limited to, any material from a list comprising polyvinylpyrrolidones, polyoxazolines, starches, polyacrylic acids, polyacrylates, poly(ethylene glycol), polyvinyl alcohols, carbomers, cellulose derivatives, polysaccharides, xanthan, pectin, guar gum, natural gums, and copolymers comprising two or more monomer types from polymers in this list.

The adhesive layer 106 can, on contact with saliva-moistened teeth and or an orthodontic implement, can offer initial adhesion of the device to the teeth and/or orthodontic implement and rapidly absorb said saliva. In some variations, adhesive layer 106 can further comprise a plasticizer. As used herein, the term "plasticizer" can refer to any substance which, when mixed a hygroscopic polymeric material, results in a mixed material of greater plasticity than that of the hygroscopic polymeric material alone. Suitable plasticizers will in many instances be hydrophilic and can include but are not limited to polyols, such as glycerin, sorbitol, xylitol, propylene glycol, and PEG 200-6000, and esters of polyols such as glycerin triacetate.

In a use position, the shield 100 can be of a length to cover some or all of the exterior surfaces of the orthodontic appliances on the upper and/or lower teeth, and prevents the engagement of the sharp edges and portions of the orthodontic appliances covered by the device 100 with the inner surfaces of the soft tissue of the user's lips or cheeks. This prevents the orthodontic appliance from causing injury to and bleeding from the lip or cheek tissue when an external force, as frequently occurs during a contact or even a non-contact athletic event, brings the soft tissue into forced engagement with the sharp edges, corners, or other portions of the orthodontic appliances.

The shield 100 thus minimizes injury to the soft tissue, which can prevent bleeding during an athletic event that previously would have required the athlete to remove himself or herself from the event until the bleeding stopped.

During use of device 100, a user can initially apply device 100 to the facial surfaces of the user's teeth and/or to one or more orthodontic implements attached thereto. In some examples, an orthodontic implement can be "braces", comprising brackets and an arch wire. In such examples, initial application would typically be performed such that surfaces 104A and 104E contact the facial surfaces of the teeth. In some such examples, brackets and arch wire would approximately fit into a longitudinal channel of device 100.

Subsequent to initial application of the device, the user can mold device 100 to teeth and braces by pinching or otherwise exerting finger pressure applied approximately at surfaces 104F, 104G, and 104H toward the teeth and/or braces at various locations along the length of device 100. During initial application, water absorption by adhesive layer 106 can produce an initial adhesion. Said initial adhesion can prevent device 100 from being pulled off during initial application and/or molding as might otherwise occur due to stickiness between device 100 and user's fingers. Additionally, moisture absorption by adhesive layer 106 can rapidly dry the braces and teeth.

Also, the device shown in FIGS. 2-4 can be modified in a variety of ways to make changes to its shape. For example, any of the surfaces 104A-104E can be curved instead of flat. The length of the device (7 mm), the depth and width of the groove (3 mm), and the widths of surfaces 104A-104E (2 mm) can also be variable, with one or more of these lengths and widths being adjusted to zero (all dimensions are examples only). As shown by comparison of FIGS. 3 and 4, any or all of the corners between surfaces 104A-104E may be square or rounded.

Figure 5:
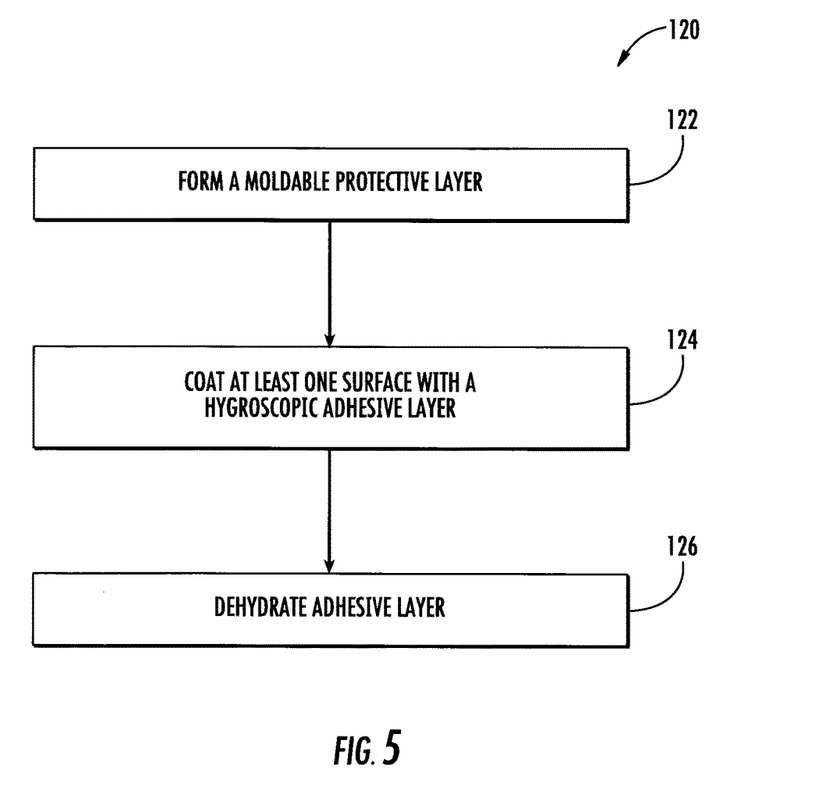
FIG. 5 is a flow chart of a method for fabricating an orthodontic protection device.

A method 120 of fabricating an orthodontic protection device is shown schematically in FIG. 5. In step 122, a protective layer 102 formed of a moldable material and suitably shaped to temporarily cover an orthodontic implement in a user's mouth is provided. In many instances a suitable shape will be one which is substantially longer in one dimension than in any other, such as relatively long, narrow cylinder or rectangular prism. In some instances, a suitable shape will be of the type shown above in FIGS. 1-4 with a longitudinal channel operable to accommodate the protrusions of an orthodontic implement. Suitable moldable materials employed in step 122 can be of the type described above.

In step 124, at least one surface of protective layer 102 is coated with an adhesive layer 106 comprising a hygroscopic polymeric material. Suitable examples of hygroscopic polymeric material are as described above. In some instances, step 126 can be performed by applying an aqueous solution of hygroscopic polymeric material to protective layer 102 and allowing said aqueous solution to dry. In many instances, hygroscopic polymeric material will be applied to one or more surfaces of protective layer 102 which are configured to contact the facial surfaces of a user's teeth and or orthodontic implement, such as surfaces 104A, 104B, 104C, 104D, and/or 104E as described above. In addition, a hydrophilic plasticizer as described above can optionally be mixed with the hygroscopic polymeric material prior to application to protective layer 102.

In optional step 126, the applied hygroscopic polymeric material, which comprises an adhesive layer 106 can be dehydrated after application in order to maximize its water absorbing ability. Such dehydration can be achieved, for example, by exposing device 100 to evaporative heat.

EXAMPLES

The following Examples are presented for illustrative purposes only and are not to be interpreted as limiting the scope of the present orthodontic protection device. The Examples will enable a clearer understanding of the characteristics and advantages of the invention.

Example 1

Three co-joined, approximately 2 inch segments of "OrthoSil Silicone Dental Wax" were coated with a thin film of an aqueous solution of polyvinylpyrrolidone and glycerin on what will become surfaces 104A-104E on the device. This was then placed into the "U"-shape shown in FIG. 1 and heated in an oven at 100° C. for one hour to drive most of the moisture from the hydrogel-forming layer.

Example 2

Three co-joined, approximately 2 inch segments of "OrthoSil Silicone Dental Wax" were coated with a thin film of an aqueous solution of poly(2-ethyl-2-oxazoline) and glycerin on what will become surfaces 104A-104E on the device. This was then placed into the "U"-shape shown in FIG. 1 and heated in an oven at 100° C. for one hour to drive most of the moisture from the hydrogel-forming layer.

Example 3

Fumed-silica-filled silicone fluid was prepared by combining 13.88 g of high-viscosity silicone fluid (polydimethylsiloxane, viscosity 2,500,000 centistokes) with 1.36 g of fumed silica (surface area 400 m2/g) at 300-400° C. A 2 inch device as illustrated in FIG. 1 was then constructed with this material. Surfaces 104A-104E were then coated with a thin film of an aqueous solution of polyvinylpyrrolidone and glycerin and heated in an oven at 100° C. for one hour to drive most of the moisture from the hydrogel-forming layer.

Example 4

OrthoSil Silicone Dental Wax was loaded into a hand extruder and extruded through a die to prepare continuous strips of variable lengths with the shape and dimensions shown in FIG. 2. Surfaces 104A-104E were then coated with a thin film of an aqueous solution of polyvinylpyrrolidone and glycerin and heated in an oven at 100° C. for one hour to drive most of the moisture from the hydrogel-forming layer.

Example 5

Dow Corning BMG silicone HCR (Biomedical Grade High Consistency Rubber) base with nominal values of 35, 50, or 65 Shore A Durometer or mixtures thereof, was loaded into a hand extruder and extruded through a die to prepare continuous strips of variable lengths with the shape and dimensions shown in FIG. 2. Surfaces 104A-E were then coated with a thin film of an aqueous solution of polyvinylpyrrolidone and glycerin and heated in an oven at 100° C. for one hour to drive most of the moisture from the hydrogel-forming layer.

The foregoing description and Examples relate to what are presently considered to be the most practical embodiments. It is to be understood, however, that the disclosure is not to be limited to these embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An orthodontic protection device comprising:
a protective layer shaped to fit over a facial surface of at least one tooth and any orthodontic appliances affixed to the facial surface of the of at least one tooth wherein composed substantially of a moldable material; and
an adhesive layer including at least one hygroscopic polymeric material;
wherein the moldable material is a plastically deformable, silicone base material chosen from the group consisting of a polydimethylsiloxane and a vinyl-functionalized polydimethylsiloxane where either or both are compounded (mixed or combined) or in a mixture with either one or both of: a silica or a trimethylated silica.

2. The orthodontic protection device of claim 1, wherein the device comprises an elongated member with opposing walls defining a longitudinal channel.

3. The orthodontic protection device of claim 2, wherein the elongated member has a substantially uniform cross-sectional configuration.

4. The method of claim 3, wherein the adhesive layer further includes a plasticizer.

5. The orthodontic protection device of claim 1, wherein adhesive layer further includes a hydrophilic plasticizer.

6. The orthodontic protection device of claim 5, wherein the hydrophilic plasticizer is a polyol or polyol ester.

7. The orthodontic protection device of claim 1, wherein subsequent to initial application, the moldable material is such that a user can mold the device to the teeth and braces to achieve a tight fit onto the orthodontic appliance by pinching or otherwise exerting finger pressure to the device without the need to apply heat to the moldable material.

8. The orthodontic protection device of claim 1, wherein the moldable material has a glass transition temperature below about 37° C.

9. The orthodontic protection device of claim 1, wherein the device comprises a shape having an outer perimeter defined by an outer rim, with a cavity region defined thereby.

10. The orthodontic protection device of claim 1, wherein the hygroscopic polymeric material comprises at least one material chosen from the group consisting of a polyvinylpyrrolidone, polyoxazoline, starch, polyacrylic acid, a polyacrylate, a polyvinyl alcohol, a carbomer, a cellulose derivative, a polysaccharide, xanthan, pectin, and guar gum, a natural gum, and copolymers comprising two or more monomer types from the polymers so listed.

11. The orthodontic protection device of claim 1, wherein the protective layer is shaped to fit over the facial surfaces of a single tooth and any orthodontic appliance or orthodontic appliances affixed to the facial surface of the single tooth.

12. A method of fabricating an orthodontic protection device comprising:
providing a moldable material suitably shaped to temporarily cover an orthodontic implement in a user's mouth, wherein the moldable material is a plastically deformable, silicone base material chosen from the group consisting of a polydimethylsiloxane and a vinyl-functionalized polydimethylsiloxane where either or both are compounded (mixed or combined) or in a mixture with either one or both of: a silica or a trimethylated silica; and
coating a surface of the moldable material with an adhesive layer which includes a hygroscopic polymer.

13. The method of claim 12 further comprising the step of dehydrating the adhesive layer.

14. The method of claim 13, wherein the step of dehydrating is via application of heat.

15. The method of claim 12, wherein the moldable material comprises a polymeric material.

16. The method of claim 15, wherein the adhesive layer further includes a hydrophilic plasticizer and the hydrophilic plasticizer is a polyol, a polyol ester, or a polyol and a polyol ester.

17. The method of claim 12, wherein the moldable material has a glass transition temperature below about 37° C.

18. The method of claim 12, wherein the moldable material comprises:
a silicone polymer compounded (mixed, combined) or in a mixture with either one or both of silica or trimethylsilylated silica.

19. The method of claim 12, wherein the hygroscopic polymer comprises:
at least one material from the group consisting of: a polyvinylpyrrolidone, a polyoxazoline, a starch, a polyacrylic acid, a polyacrylate, a polyvinyl alcohol, a carbomer, a cellulose derivative, xanthan, pectin, guar gum, a natural gum, and copolymers comprising two or more monomer types from any of above.

20. An orthodontic protection device comprising:
a protective layer shaped to fit over a facial surface of at least one tooth and any orthodontic appliances affixed to the facial surface of the of at least one tooth wherein composed substantially of a moldable material; and
an adhesive layer including at least one hygroscopic polymeric material applied to the protective layer on a surface opposite the facial surface;
wherein the moldable material is a plastically deformable, silicone base material chosen from the group consisting of a polydimethylsiloxane and a vinyl-functionalized polydimethylsiloxane where either or both are compounded (mixed or combined) or in a mixture with either one or both of: a silica or a trimethylated silica.

21. The orthodontic protection device of claim 20, wherein the adhesive layer further comprises a hydrophilic plasticizer.

* * * * *